Figure 1:
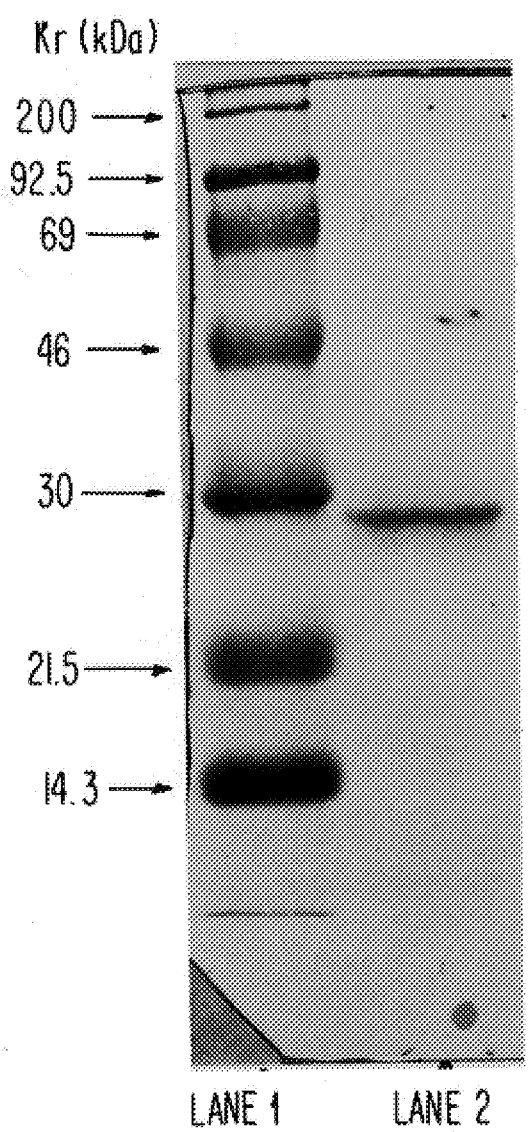

United States Patent [19]
Flodgaard et al.

[11] Patent Number: 5,814,602
[45] Date of Patent: Sep. 29, 1998

[54] HEPARIN-BINDING PROTEINS

[75] Inventors: Hans Flodgaard, Hellerup; Erik Ostergaard, Vanlose; Johannes Thomsen, Kokkedal; Stephen Bayne, Roskilde, all of Denmark

[73] Assignee: Novo Nordisk A/S, Bagsvaerd, Denmark

[21] Appl. No.: 470,841

[22] Filed: Jun. 6, 1995

Related U.S. Application Data

[63] Continuation of Ser. No. 994,053, Dec. 15, 1992, abandoned, which is a continuation of Ser. No. 583,393, Sep. 17, 1990, abandoned, which is a continuation-in-part of Ser. No. 325,138, Mar. 17, 1989, abandoned.

[30] Foreign Application Priority Data

Mar. 17, 1988 [DK] Denmark .................................. 1453/88
Feb. 17, 1989 [DK] Denmark .................................... 737/89

[51] Int. Cl.$^6$ ........................ A61K 38/17; A61K 38/18; C07K 14/47; C07K 14/515
[52] U.S. Cl. .............................. 514/8; 514/21; 530/380; 530/395
[58] Field of Search .................................... 530/350, 380, 530/381, 395; 517/8, 21

[56] References Cited

U.S. PATENT DOCUMENTS

| | | | |
|---|---|---|---|
| 5,026,639 | 6/1991 | Johnson | 530/380 |
| 5,087,569 | 2/1992 | Gabay et al. | 530/350 |
| 5,458,874 | 10/1995 | Pereira et al. | 424/85.1 |
| 5,484,885 | 1/1996 | Pereira et al. | 530/326 |

FOREIGN PATENT DOCUMENTS

| | | |
|---|---|---|
| 0241136 | 10/1987 | European Pat. Off. . |
| 0298723 | 1/1989 | European Pat. Off. . |
| 8603122 | 6/1986 | WIPO . |
| 8707183 | 12/1987 | WIPO . |
| 8810269 | 12/1988 | WIPO . |

OTHER PUBLICATIONS

Shafer et al., Infection and Immunity, vol. 45, No. 1, pp. 29–35 (1984).

Shafer et al., Infection and Immunity, vol. 53, No. 3, pp. 651–655 (1986).

Dialog Information Services, File 55, BIOSIS 81–89, BIOSIS No. 79028069, Raugi G J et al.: "Location and partial characterization of the heparin–binding fragment of platelet thrombospondin", Thromb Res 36(2), 1984, 165–176.

PCT International Preliminary Examination Report, pp. 1, 1A and 3 and PCT claims 1–17, 1990.

Dialog Information Services, File 55, BIOSIS 81–89, BIOSIS No. 85050038, Rauvala H et al: "Isolation and some characteristics of an adhesive factor of brain that enhances neurite outgrowth in central neurons", J Biol Chem 262(34), 1987, 16625–16635.

Dialog Information Services, File 55, BIOSIS 81–89, BIOSIS No. 83082612, Pande H et al: Demonstration of structural differences between the two subunits of human–plasma fibronectin in the carboxyl–terminal heparin–bindnng domain Eur J Biochem 162(2), 1987, 403–412.

Dialog Information Serivces, File 55, BIOSIS 81–89, BIOSIS No. 79028069, Raugi G J et al: "Location and partial characterization of the heparin–binding fragment of platelet thrombospondin", Thromb Res 36(2), 1984, 165–176 . . . / . . .

Sally W. Hennessy, Complete Thrombospindin mRNA Sequence Includes Potential Regulatory Sites in the 3'Untranslated Region pp. 729–735, J. Cell. Biol. vol. 108 (1989).

(List continued on next page.)

*Primary Examiner*—Jeffrey E. Russel
*Attorney, Agent, or Firm*—Steve T. Zelson; Cheryl H. Agris

[57] ABSTRACT

A heparin-binding protein (HBP) which has, in glycosylated state, an apparent molecular weight of about 28 kDa, determined by SDS-PAGE under reducing conditions, and exhibits angiogenic properties in vivo.

10 Claims, 6 Drawing Sheets

OTHER PUBLICATIONS

Eur. J. Biochem., vol. 197, issued 1991, Flodgaard et al, "Covalent Structure of Two Novel Neutrophilin", pp. 535–547.

Lawler et al., Thromb. Res., vol. 22, pp. 267–279 (1981).

Petersen et al., J. Urology, vol. 142, pp. 176–180 (1989).

Pande et al, Eur. J. Biochem. vol. 162 (2) pp. 403–412 (1987).

Rauvala et al., J. Biol. Chem., vol. 262 No. 34 pp. 16625–16635 (1987).

Raugi et al., Thromb. Des., vol. 36 pp. 165–175 (1984).

Chodale et al, Cancer Res., vol. 46 pp. 5507–5510 (1986).

Pereira et al., J. Clin. Invest., vol. 85 pp. 1468–1476 (1990).

Pohl et al., FEBS Lett., vol. 272, No. 1, 2, pp. 200–204 (1990).

Wilde et al., J. Biol. Chem., vol. 265 pp. 2038–2041 (1990).

Gabay et al., PNAS USA, vol. 86 pp. 5610–5614 (1989).

Chodak et al., Cancer Res., vol. 46(11) pp. 5507–5510 (1986).

Neurath et al, "The Proteins", $3^{rd}$ ed., published 1975 by Academic Press (NY), vol. I, pp. 179, 180, and 191.

HEPARIN-BINDING PROTEINS

This is a continuation of application Ser. No. 07/994,053 filed on Dec. 15, 1992, now abandoned, which is a continuation of application Ser. No. 07/583,393 filed Sep. 17, 1990 (now abandoned) which is a continuation-in-part of application Ser. No. 07/325,138 filed Mar. 17, 1989 (now abandoned).

The present invention concerns heretofore unknown heparin-binding proteins or equivalent modifications hereof which release angiogenesis and improve granulation tissue formation in wounds in animal models. The invention also relates to processes for producing the proteins and pharmaceutical preparations containing the proteins suitable for stimulation of tissue repair in man, in particular for topical application to external wounds. The proteins are furthermore characterized by in the normal condition being glycoproteins.

Normal tissue repair follows an orderly sequence of cellular and biochemical events, which is initiated by injury and results in new tissue formation.

Resting fibroblasts at the wound edge divide, migrate towards the avascular wound space, and produce collagen. New capillaries bud from preexisting venules and capillaries and migrate towards the wound edge. These processes continue until the edge of the healing wound fuses, filling the wound space with a vascularized collagen fibroblast mesh (granulation tissue). Finally, epithelial cells divide and cover the granulation tissue and the repair process is finished.

The blood platelets are the first cellular element of importance for the healing of an acute wound within the first 24 hours. Then the healing processes are taken over by neutrophilic granulocytes followed by macrophages and lymphocytes, which can all be seen to migrate into the wound in an orderly sequence during the next 2 to 3 days after the tissue damage. It is these inflammatory cells which eventually ensure correct healing via carefully adapted release of paracrinic growth factors In recent years some understanding has accumulated concerning the mechanism for the action for these growth factors, which are called Platelet derived growth factor (PDGF), Transforming growth factor alpha (TGF$\alpha$), and Transforming growth factor $\beta$ (TGF$\beta$) in the wound healing process. PDGF is initially released from the a-granules of the blood platelets when the platelets adhere to the edges of the fresh wound and have strong chemotaxis for fibroblasts (Grotendorst, G.R. et al. (1981). Proc. Natl. Acad. Sci. USA. 78: 3669–3672) in addition to being mitogenic to the same cells in the presence of either TGF$\alpha$ or epidermal growth factor (EGF) (Deuel, T.F. et al. (1985) Cancer Surv. 4: 633–653).

PDGF activates fibroblasts to release collagenase (Bauer, E. A. et al. (1985) Proc. Natl. Acad. Sci. USA, 82: 4132–4136) and thus contributes to remodelling the matrix, an essential element in the wound healing.

TGF$\beta$ is found in relatively high concentrations in the blood platelets and is also shown to be released from a granules during the clot formation. This growth factor plays an important part in the matrix formation in wounds and has also been found to have a regulatory influence on a variety of other growth factors, such as PDGF, EGF, and TGF$\alpha$.

TGF$\beta$ exhibits strong chemotactic activity for monocytes. Thus the growth factors initially released from platelets immediately after wounding also play an important role by stimulating migration of inflammatory cells to the wound. TGF$\beta$ may recruit monocytes from the circulation and subsequently activate them to the secretory phenotype (Wiseman, D. M. et al. (1988) Biochemical and Biophysical Research Communications 157, 793–800).

Once the monocytes have obtained this phenotype and are now better named macrophages, they can be shown to secrete the same factors found in platelets plus several others of great importance to the repair process.

Thus monocytes/macrophages excrete growth regulatory factors, such as Platelet derived growth factor (PDGF), Transforming growth factor beta (TGF$\beta$), Transforming growth factor alpha (TGF$\alpha$), Basic fibroblast growth factor (BFGF), Insulin-like growth factor one (IGF-1) Bombesin, Granulocyte-stimulating factor (GSF), Granulocyte-macrophage colony stimulating factor (GM-CSF), Monocyte stimulating factor (M-CSF) and Interleukin-1 (IL-1). The secretory products also include proteases, complement proteins, monocyte-derived neutrophil-activating factor, arachidonates and Tumor necrosis factor alpha (TNF$\alpha$). (Rom, W. N. et al. (1988) J. Clin. Invest. 82, 1685–1693), (Rappolee D. A. et al (1988) Science 241, 708–712), (for review see Unanue, E. R. et al (1987). Science 236, 551–557).

All these macrophage derived paracrinic growth factors participate in the healing process, but many details concerning the mechanism and the complex interaction among these factors are still poorly understood.

During the healing process it is of decisive importance that the growing tissue is sufficiently provided with oxygen and nutrients. This is secured by the complicated process known as angiogenesis which leads to formation of new blood vessels in situ. This process involves the orderly migration, proliferation and differentiation of vascular cells, (Folkman, M. et al. (1987). Science 235, 442). The initiation of angiogenesis by direct stimulation of endothelial cell proliferation is the presumed responsibility of two polypeptide mitogens: The class I heparin-binding growth factor (HBGF-1), also known as acidic fibroblast growth factor, and class II heparin-binding growth factor (HBGF-II) or basic fibroblast growth factor (BFGF) (Thomas, K. A. (1985). Proc. Natl. Acad. Sci. 82, 6409), (Esch, F. (1985) ibid: 6507). These factors are not found in platelets, but basic FGF is secreted from activated monocytes/macrophages as mentioned above and have been shown to induce angiogenesis in animal models in vivo.

It is therefore clear that the initial "burst" of platelet release in connection with wounding does not involve direct angiogenic factors. However, platelet extracts are shown to be angiogenic in in vivo experiments and this can be shown to be a result of monocyte activation which in turn leads to secretion of the relevant factors mentioned above. Several attempts to isolate and characterize a non-mitogenic angiogenic factor in platelets have been done, but the nature of this factor is not disclosed in the arts (Knighton, D. R. et al., 1986, Ann. Surg. 204, 323–331).

A necessary requisite for angiogenesis to occur is the presence of heparin in the wound area, and it has been shown that removal of heparin with e.g. protamine completely abolishes angiogenesis.

Therefore any factor having the capability of recruiting monocytes from the circulation to the wounded area and subsequently activating them in addition to having heparin-binding properties, must be of extreme importance for angiogenesis and the whole repair process as well.

The present invention provides heretofore unkown proteins (the human and porcine types are hereinafter referred to as hHBP and pHBP) which are uniquely suited to stimulate anqiogenesis and tissue repair for the following reasons:

a) The proteins are released from platelets when these cells are activated such as it occurs in the damaged tissue.
b) The proteins bind to heparin.
c) The proteins are chemotactic for monocytes.
d) The proteins activate monocytes morphologically towards the secretory phenotype.
e) The proteins activate monocytes in culture to excrete mitogens for fibroblasts in culture.
f) Application of the proteins gives rise to angiogenesis in the hen egg chorio-allantoic membrane model.
g) The proteins increase epithealization rate when applied to wound-chambers in experimental models in rats judged from macroscopic and histological examinations.
h) The proteins increase granulation tissue formation in the same wound-chamber model judged from macroscopic and histological examinations.
i) The proteins increase blood vessel formation in the same rat wound-chamber model judged from macroscopic examinations.

Two specific examples of hitherto unknown proteins are derived from porcine and human platelets the amino acid sequence of the porcine type has been fully elucidated as disclosed below. The human type is strongly homologous to the porcine type as evident by comparing the amino acid sequence of the porcine type as disclosed with the amino acid sequence for the human type.

An important feature in relation to tissue repair is the strong heparin-binding properties of the proteins. Shortly after tissue damage it can be observed that connective tissue mast cells among several components of importance for the inflammation also release large amounts of heparin. (Qureshi, R. et al. (1988). The Journal of Immunology 141, 2090–2096).

The released heparin is known to bind to collagen and once this has been established, the heparin-binding proteins (HBP) described in this invention thereby become immobilized. This can form a fixed gradient and as Gustafson et al. have suggested on theoretical grounds and Carter has shown experimentally, cells tend to move up a gradient of increasing substrate adhesion. Carter has suggested that this phenomenon should be called "Haptotaxis" (Greek: haptein, to fasten; taxis, arrangement). On this basis, the cell migration involved in morphogenesis, inflammation, wound healing, tumour invasion and indeed all tissue cells movements, are considered to be the result of haptotactic responses by the cells involved (Gustafson, T. et al. (1963). Intern. Rev. Cytol, 15, 139), (Carter, S. B. (1965), Nature 208, 1183–1187).

On this basis the heparin-binding proteins herein are uniquely suited to recruit monocytes from the circulation into the damaged tissue area. The subsequent activation to secretory phenotype takes place in situ i.e. the complete cocktail of monocyte/macrophage derived cytokines releases in the neighbourhood of the damaged cells in the wound and faciliates healing The heparin-binding proteins herein are foreseen especially to be suitable to stimulate healing of chronic wounds in man. It is generally believed that the most important pathogenic factor for the chronic leg ulcers and decubitus in elderly patients is the lack of neovascularization (angiogenesis).

On the basis of the properties mentioned for the heparin-binding proteins external application of the proteins (preferably the human type) to chronic wounds are foreseen to accelerate healing. Ablation of macrophages slows the wound-healing response (Leibovich, S. J. et al. (1975). Am. J. Pathol. 78, 71). In the human clinic such depletion of macrophages accompanies several illnesses, and it is also often a result of therapy. Thus, severe leucocytopenia is observed in cancer patients treated with chemotherapy or radiation therapy. Slow healing after surgical treatment and occurrence of chronic ulcers is often seen in such patients. The special properties shown by the heparin-binding proteins may be of therapeutic benefit in such patient groups.

HBP may also be used in the therapy of severe burns. The lack of neovascularization results in poor healing and the damaged tissue is susceptible to infections. Therefore, a component having monocyte activating properties may be of great advantage. Activated monocytes or "macrophages" act as scavengers, and by phagocytosis they remove damaged tissue debris, a most essential function in connection with burns.

More recently, the growth regulatory role of macrophages with respect to tumor growth has received considerable attention.

High concentrations of activated macrophages are cyostatic to neoplastic cells, and this effect is directed selectively against neoplastic target cells. The putative secretory product from macrophages in this context is believed to be TNFα (Diegelmann, R. F. et al. 1981, Plastic and Reconstructive Surgery 1968, 107–113)

The heparin-binding proteins herein may have therapeutic possibilities in tumor therapy. HBP injected to solid tumors can recruit circulating monocytes to the tumor area and by subsequent activation mediate cytotoxic effect.

Pharmaceutical compositions for use in the present invention in the clinic as suggested above include incorporation of human HBP into creams, ointments, gels, foams, dressing materials, patches, pads, artificial skins, aqueous vehicles for soaking gauze dressing, dry swellable powders or suture coatings.

The formulations which may be used to entrap HBP are a freeze-dried pad or a hydrocolloid occlusive dressing. It is preferred that a medical dressing which provides controlled release of HBP is used.

The gel which may be used consists of an aqueous basis which is made highly viscous by adding water-soluble etherified cellulose derivatives such as alkyl cellulose, hydroxyalkyl cellulose and alkylhydroxyalkyl celluloses, e.g. methyl cellulose, hydroxyethyl cellulose, carboxymethyl cellulose, hydroxypropylmethyl cellulose and hydroxypropyl cellulose. The hydroxyalkyl cellulose derivatives, such as hydroxypropyl cellulose, hydroxyethyl cellulose and hydroxypropylmethyl cellulose are preferred. Usually HBP is dissolved in the aqueous phase before the gelling agent is added.

A freeze-dried pad may consist of a hydroxycolloid with a coherent fibrous structure formed by lyophilization of a gel. The hydrocolloid may be a water-soluble etherified cellulose derivative as mentioned above. Usually HBP is entrapped in the pads prior to freeze-drying.

A medical dressing may be an adhesive occlusive bandage having HBP incorporated in it. The dressing comprises a sealing material, a tackifier as a continuous phase, and a discontinuous phase dispersed in the continuous phase which comprises one or more water-soluble or water-swellable compounds, such as etherified cellulose derivatives mentioned above. The ability of the discontinuous phase to swell in water gives the possibility of gradual release of previous physically entrapped HBP. HBP may also be administered in liquid formulations by subcutaneous, intermuscular or intravenous injections. Furthermore, the administration of HBP may also occur by nasal, buccal, rectal or intraperitoneal routes.

According to the invention, HBP can be produced from blood platelets, obtained from porcine or human blood. More particularly, the protein is produced by fractionation of a blood platelet extract. Column chromatography using a HEPARIN-SEPHAROSE® (pharmacia) gel sizing column is expedient for this purpose. Such a chromatographic method comprising gradient elution with NaCl from 0.5M up to 3M of a column through which an extract of the blood platelets has been poured first, results in elution of two peaks. The first peak around 1.2M NaCl can be measured at 280 nm as a large protein peak and is a platelet factor ($PF_4$) known per se. Around 1.8M NaCl, the protein amount is below the detection limit in the system used, but the fractions in this area have angiogenic activity. The active fractions are purified additionally by microbe reverse phase HPLC on $C_4$ column, and at 21.4 nm a completely pure protein peak can be detected, and this protein is identical with the present HBP's of either porcine or human type depending on the kind of platelets used.

The HBP's may also be produced by recombinant technique. Bacteria, yeasts, fungi or mammalian cell lines may be used as hosts for the production of HBP. By transformation of the host cell with a suitable vector containing the necessary transcription and translation signals as well as the DNA-sequence encoding HBP, production of HBP can be achieved.

A choice can be made as to whether the product should be produced intracellularly or secreted to the growth medium. Many secretion signals are known. U.S. Pat. No. 4 336 336 describes for procaryotes the use of a leader sequence coding for a non-cytoplasmic protein normally transported to or beyond the cell surface resulting in transfer of the fused protein to the periplasmic space. For yeasts, Kurjan & Herskowitz, Cell (1982), 30, 933–943 describes a putative α-factor precursor containing four tandem copies of mature α-factor, describing the sequence and postulating a processing mechanism. This signal sequence has been used for the secretion of a wide variety of polypeptides from the yeast Saccharomyces cerevisiae ever since the discovery of the signal sequence. Brake et al, PNAS USA, 81, (1984) 4642–4646 gives one example hereof.

Bacteria are not capable of either glycosylating proteins or, in most cases, forming the correct disulphide bridges in polypeptides of human origin.

Yeast, however, can form correct disulphide bridges, but does not glycosylate proteins in the same manner as higher eucaryotes do. Yeast mutants have been isolated, which glycosylate in a manner similar to mammalian cell lines, thus making yeast a useful host for glycosylated proteins in the future.

The present HEP's are moreover characterized in that they migrate as single bands in SDS-PAGE under reducing conditions, (depicted in FIGS. 1 and 2 ) and have a $M_r$ of about 28 kDa.

Heparin-binding protein purified from porcine blood platelets may have the following amino acid sequence

```
 1         5              10              15
Ile-Val-Gly-Gly-Arg-Arg-Ala-Gln-Pro-Gln-Glu-Phe-Pro-Phe-Leu-Ala-Ser-
                                                              20
                                                       -Ile-Gln-Lys- 21             25              30              35
Gln-Gly-Arg-Pro-Phe-Cys-Ala-Gly-Ala-Leu-Val-His-Pro-Arg-Phe-Val-
                                                              40
                                                       -Leu-Thr-Ala-Ala-
 41             45              50              55
Ser-Cys-Phe-Arg-Gly-Lys-Asn-Ser-Gly-Ser-Ala-Ser-Val-Val-Leu-Gly-
                                                              60
                                                       -Ala-Tyr-Asp-Leu- 61             65              70              75
Arg-Gln-Gln-Glu-Gln-Ser-Arg-Gln-Thr-Phe-Ser-Ile-Arg-Ser-Ile-Ser-Gln-
                                                              80
                                                       -Asn-Gly-Tyr-
 81             85              90              95
Asp-Pro-Arg-Gln-Asn-Leu-Asn-Asp-Val-Leu-Leu-Leu-Gln-Leu-Asp-Arg-
                                                             100
                                                       -Glu-Ala-Arg-Leu-
                                              CHO
101            105             110              \  115
Thr-Pro-Ser-Val-Ala-Leu-Val-Pro-Leu-Pro-Pro-Gln-Asx-Ala-Thr-Val-
                                                             120
                                                       -Glu-Ala-Gly-Thr-
121            125             130
Asn-Cys-Gln-Val-Ala-Gly-Trp-Gly-Thr-Gln-Arg-
                                   135             140
                           -Leu-Arg-Arg-Leu-Phe-Ser-Arg-Phe-Pro-
        CHO
141      \      145             150
Arg-Val-Leu-Asx-Val-Thr-Val-Thr-Ser-Asn-Pro-
                                   155             160
                           -Cys-Leu-Pro-Arg-Asp-Met-Cys-Ile-Gly-
161            165             170
Val-Phe-Ser-Arg-Arg-Gly-Arg-Ile-Ser-Gln-Gly-
                                   175             180
                           -Asp-Arg-Gly-Thr-Pro-Leu-Val-Cys-Asn-
181            185             190             195
Gly-Leu-Ala-Gln-Gly-Val-Ala-Ser-Phe-Leu-Arg-Arg-Arg-Phe-Arg-Arg-
                                                             200
                                                       -Ser-Ser-Gly-Phe-
201            205             210             215
Phe-Thr-Arg-Val-Ala-Leu-Phe-Arg-Asn-Trp-Ile-Asp-Ser-Val-Leu-Asn-
                                                             219
                                                       -Asn-Pro-Pro.
```

Heparin-binding protein purified from human platelets may have the following amino acid sequence:

```
 1                                                                 20
Ile — Val — Gly — Gly — Arg — Lys — Ala — Arg — Pro — Arg — Gln — Phe — Pro — Phe — Leu — Ala — Ser — Ile — Gln — Asn
```

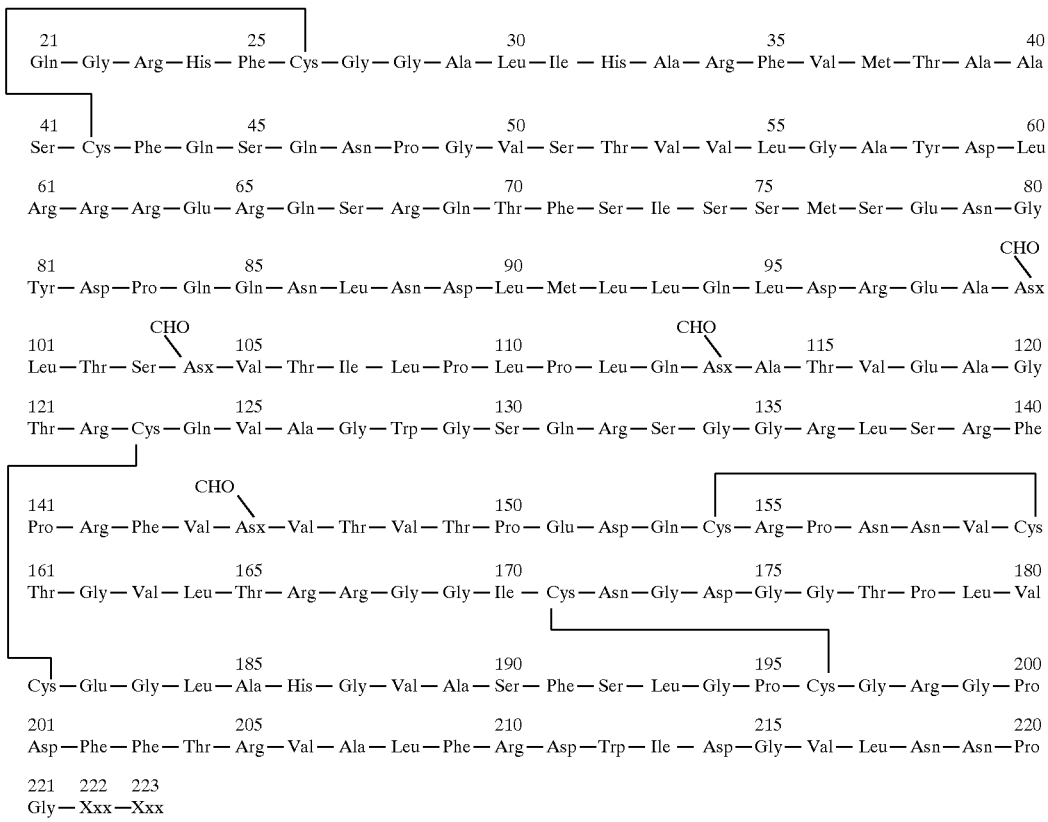

wherein Xxx at 222 is Pro or absent, and Xxx at 223 is Gly or absent.

The invention will be explained by the following examples:

LEGEND TO FIGURES

Figure 2:
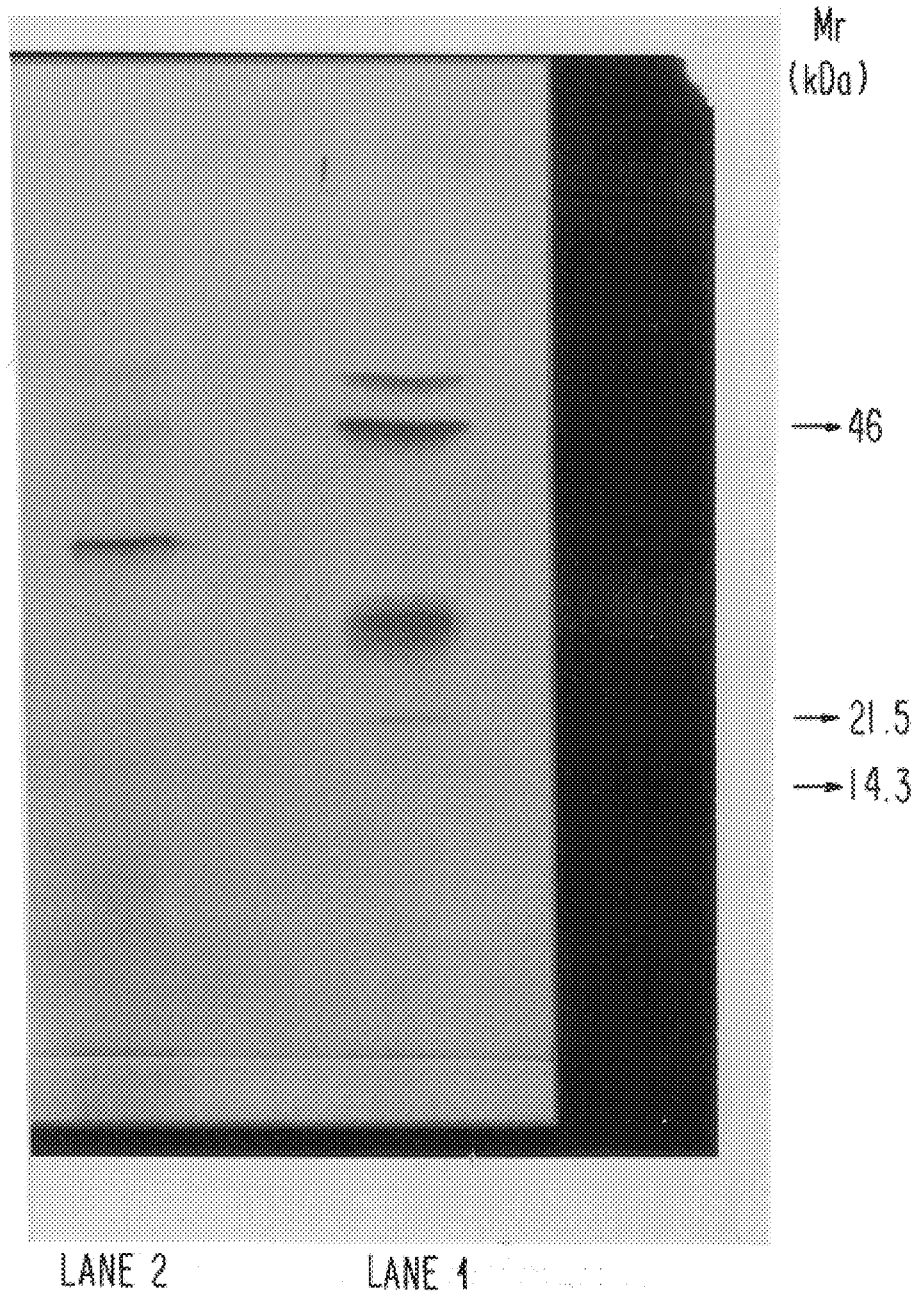

FIG. 1 SDS-PAGE under reducing conditions of heparin-binding protein of the porcine type. Lane 1: Mr markers Lane 2: pHBP FIG. 2 SDS-PAGE under reducing conditions (see Example 2) of heparin-binding protein of the human type. Lane 1: Mr markers Lane 2: hHBP FIG. 3 Test for angiogenesis for HBP by using the chick embroyo chorioallantoic membrane. For explanation, see Example 5.

Figure 4:
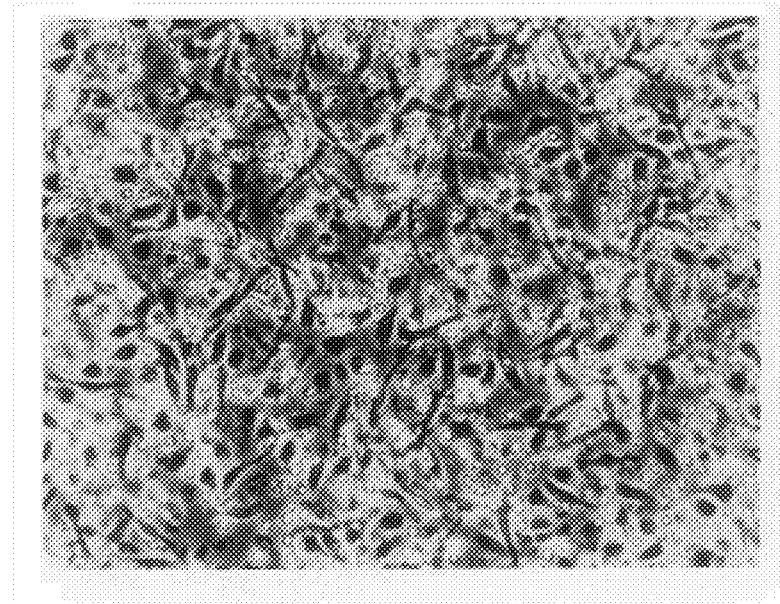
Figure 5:
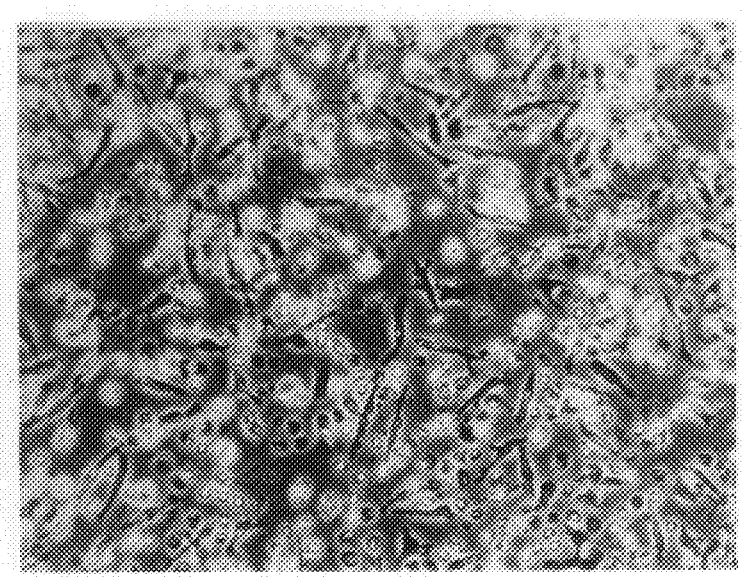
Figure 6:
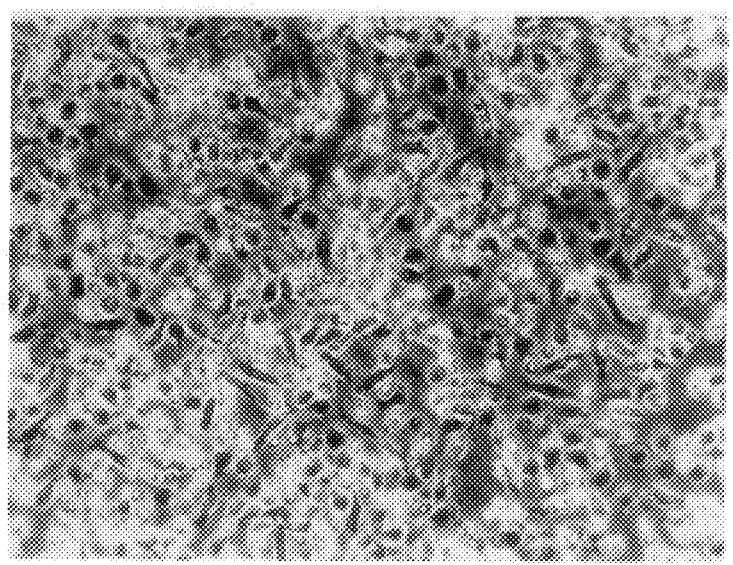

FIGS. 4, 5 and 6 In these pictures HBP treated monocytes (8 ng/ml) (FIG. 4), Endotoxin-treated monocytes (100 ng/ml) (FIG. 5) and PBS-treated monocytes (control cells) (FIG. 6) are shown. For explanation, see Example 6.

EXAMPLE 1

500 g of blood platelets from porcine blood were suspended in 1.5 l of PBS, frozen and thawed three times by means of liquid nitrogen ($N_2$), called Freeze/Thaw below. Freeze/Thaw was centrifuged at 40,000 ×g for 30 minutes, and the resulting supernatant was subjected to ultracentrifugation at 300,000 ×g for 60 minutes. The resulting supernatant was dialysed for 48 hours against 20 volumes of 10 mM phosphate buffer, 0.5M NaCl , pH 7.4. The dialysate was pumped on a 5 cm (I.D.) ×10 cm HEPARIN-SEPHAROSE® Cl-4B gel sizing column (pharmacia & upjohn) with a flow of 120 ml/h. The column was washed with the same buffer as the sample was dialysed against (buffer A) until no more protein eluted. The column was then eluted with a linear gradient from buffer A to buffer B=10 mM phosphate buffer, 3M NaCl, pH 7.4 for 20 hours with a flow of 1.7 ml/min. 200 fractions (during 6 min. each) were collected, and the angiogenic effect was tested. 50 fractions distributed symmetrically around the 1.8M NaCl fraction in the gradient showed activity. These fractions were pooled and admixed with ovalbumin until a concentration of 0.5 mg/ml. the pooled fractions were dialysed against 20 volumes of buffer A and then pumped on an 0.6 ml HEPARIN-SEPHAROSE® Cl-4B column gel sizing column (pharmacia & upjohn) with a flow of 6 ml/h. The column was eluted with a linear gradient for 10 hours with a flow of 0.04 ml/min. 120 fractions of 200 µl each were collected and tested for angiogenic activity and then pooled. The pooled fractions were then chromatographed on a reverse phase $C_4$ column (0.1 ml volume) with a linear gradient from 0 to 80% acetonitrile containing 0.1% trifluoroacetic acid (TFA) for 30 minutes with a flow of 0.025 ml/min. The angiogenic activity was detected in a base line separated top with a retention time of 26 minutes. SDS-PAGE under reducing conditions shows (see FIG. 1) that the peak contains one component (HBP) $M_r$ of 28 kDa. The protein in the same peak has the sequence stated in claim 4.

EXAMPLE 2

Production of HBP from human blood platelets 100 portions of fresh produced thrombocyte concentrates from healthy blood donors were mixed, and the thrombocytes centrifuged down at 1700 g for 15 min. at 25° C.

The thrombocytes centrifuged down were suspended in 3 volumes of PBS, and the suspension was frozen and thawed 6 times in liquid $N_2$. The suspension was then centrifuged at 40,000 g for 60 min. Supernatants from this were dialyzed for 2 days against 20 volumes of 10 mM phosphate buffer, 0.5M Nacl, pH 7.4. The dialysate was pumped on a 5 cm (I.D.) ×10 cm HEPARIN-SEPHAROSE® Cl-4B gel sizing column (pharmacia & upjohn) with a flow of 50 ml/h. The column was washed against the same buffer as the sample was dialysed against (buffer A) until no more protein eluted. The column was the eluted with a linear gradient from buffer A to buffer B=10 mM phosphate buffer, 3M NaCl, pH 7.4 for 20 hours with a flow of 0.90 ml/min. 200 fractions (of 6 min. each) were collected. The fractions were examined by Microbore Reversed Phase $C_4$ column (Aquapore Butyl 100×2.1 mm, 7 µm Brownlee Labs) with a gradient as follows:

| Time | buffer A 0.1% TFA | buffer B 70% CH$_3$CN 0.085% TFA | Flow |
| --- | --- | --- | --- |
| 0–5 min. | 60% | 40% | 200 ul/min. |
| 0–40 min. | 30% | 70% | 200 ul/min. |

The apparatus was an Applied Biosystems 130 A Analyzer, and the protein was monitored at 214 nm. Peaks with a retention time of 20 min. were collected. After drying, the samples were diluted in 0.1M Tris-Cl, 1 mM EDTA 2.5% SDS, 0.01% bromophenyl blue, 5% 2-mercaptoethanol pH 8.0. After 5 minutes at 95° C., the samples were subjected to SDS PAGE by means of Pharmacia Phast Gel equipment with SDS Phast Gel (8–25%) gels and SDS buffer strips.

The samples were run at 250 V at 10 mA at 15° C. in 60 Vh. (13). The fractions from 70–120 showed a band with $M_r$28,000. These fractions were pooled and dialysed with 20 volumes of buffer A. The dialysate was pumped on 1 ml HEPARIN-SEPHAROSE® Cl-4B gel sizing column (pharmacia & upjohn) and the column was eluted with a linear gradient from buffer A to buffer B for 10 hours with a flow of 0.04 ml/min. Fractions of 200 µl (120) were collected.

EXAMPLE 3

Production of HBP from human material.

For this purpose, a human cell line, K562, is used. This cell line, which originates from a chronic myeloid leukemia patient can be caused to differentiate in mega-karyoblastic direction, which is a precursor of the circulating blood platelets, with 12-0-tetradecanoyl phorbol-14-acetate (TPA). Alitalo et al. (12) has shown that the gene for PDGF is induced in these cells when they are treated with TPA.

K562 cells were cultivated in 175 cm$^3$ Nuclone bottles in RPMI 1640 medium supplemented with 10% fetal calf serum and antibiotics. The cell density was adjusted to 300,000 cells per ml, and TPA (Sigma) dissolved in DMSO was added until a concentration of 3 nM. After 3 days, the cells were sedimented by centrifugation at 500 ×g and then washed 1 time in 10 volumes of PBS followed by resedimentation.

10 g of cells harvested in this manner were admixed with 3 volumes of PBS, and the suspension was frozen and thawed 6 times in liquid $N_2$. The suspension was ultracentrifuged at 300,000 ×g for 60 minutes, and the supernatant was then diluted at 300 ml with 10 mM Na-phosphate buffer pH 7.4 containing 0.5M NaCl. The diluted sample was pumped on an 0.5 ml HEPARIN-SEPHAROSE® gel sizing column (pharmacia & upjohn) within 72 hours. The column was then eluted with a linear gradient for 10 hours from the application buffer (buffer A) to buffer B=10 mM Na-phosphate buffer pH 7.4 containing 3M NaCl, and 120 fractions of 200 µl each were collected.

4 fractions, symmetrical around 1.8M NaCl, were separately chromatographed on Microbore Reversed Phase $C_4$ column (Aquapore Butyl 30×2.1 mm, 7 µm, Brownlee Labs) with a linear gradient from 0 to 80% acetonitrile for 30 minutes admixed with 0.1% trifluoroacetic acid (TFA) and a flow of 25 µl/min.

A protein peak with a retention time of 26 minutes is identical to the retention time for the porcine HBP.

EXAMPLE 4

Detection of angiogenic properties for HBP.

Male rats of the Wistar family CRL:(W1)BR having a weight of about 240 g and being 80 days old were used. The rats were acclimatized 6 days before use at 21 ±1° C., 60±10% relative humidity with air change 10 times per hour and light from 6.30 a.m. to 6.30 p.m. The rats were kept in plastic cages with sawdust in the bottom. They were fed ad libitum with Altromin diet 1324 and had free access to drinking water.

The rats were anaesthetized with pentobarbital 50 mg/kg body weight by intraperitoneal injection. The rats were shaved on the back and disinfected. Through a 3 cm dorsal cut, the left kidney was exposed, and HBP, absorbed in advance in 10 µl of AFFI/GEL® Blue affinity column, 100–200 mesh (wet) 75–150µ (Bio-Rad) in both occurrences dried on a 3×3 mm GELFILM® absorbable gelatin film (pharmacia & Upjohn) was laid below the fibrous capsule of the kidney by a small incision. The surface wound was closed by 5 silk sutures, and TEMGESIC® (buprenorphin, obtained from Reckitt & Colman was given postoperatively, 0.1 ml dosed twice daily for three days. 5 days postoperatively, the rats were anaesthetized again with pentobarbital, and the left kidney was exposed. The region around the implant showed clear new vessel formation by macroscopic evaluation.

EXAMPLE 5

Test for angiogenesis for porcine and human HBP by using the chick embryo chorioallantoic membrane.

Fertilized chick eggs on the first day of gestation were placed in a humidified, 37° C. incubator. At day 7 a hole was made in the blunt end of the egg using a 25GS/8 0.5 ×16 needle, and incubation continued. At day 9 a 1 cm ×1 cm "window" was cut through the shell in the pointed end of the eggs and the windows were covered with TEGADERM® (polyurethane film with adhesive polyacrylate, obtained from 3M corporation). Incubation was continued and at day 11 HBP (5–30ng), absorbed in advance in 3 µl of AFFI/ GEL® Blue affinity column, 100–200 mesh (wet) 75–150µ (Bio-Rad) in both occurrences dried under laminar airflow on a 3×3 mm sterile GELFILM® absorbable gelatin film (pharmacia & upjohn), was laid on the choriollantoic membrane with the affigel towards the membrane and the window was closed again using TEGADERM® (polyurethane film with adhesive polyacrylate, obtained from 3M corporation). After 5 days of incubation at 37° C. the responses were microscopically assessed.

Figure 3:
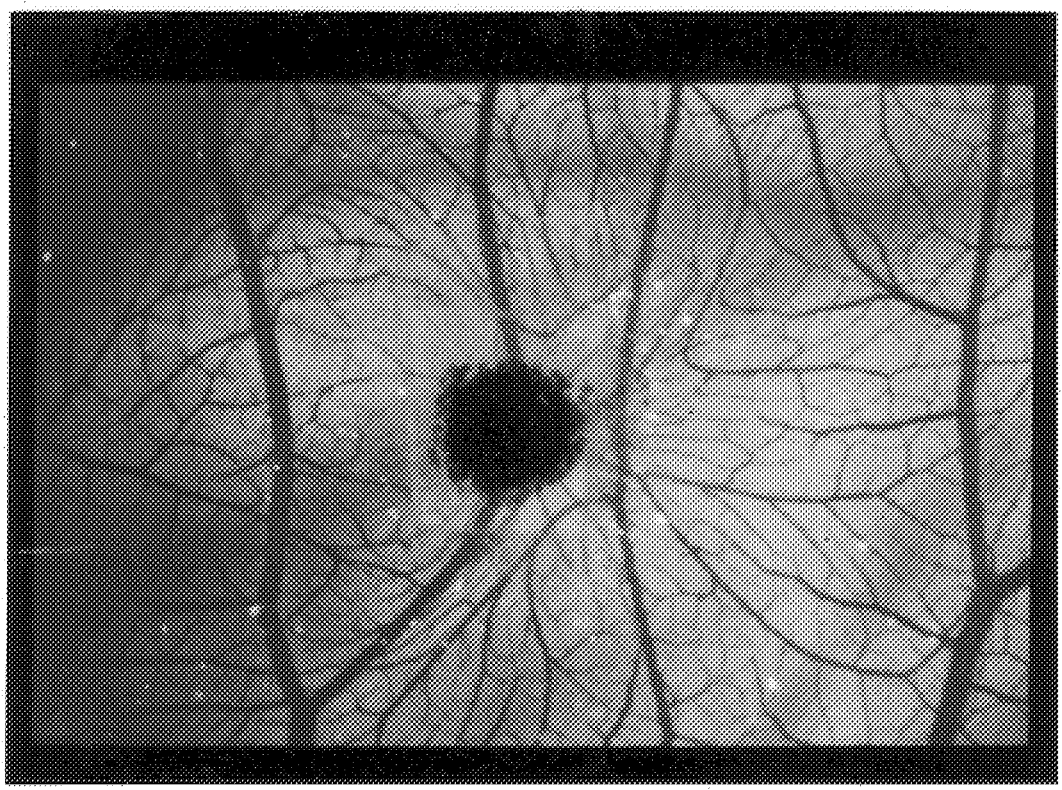

Both 30 and 5 ng HBP induced a strong increase in the density of the microvascular bed in the region of the affigel, with apparent regression of larger vessels and typical capillary-ball formations FIG. 3.

EXAMPLE 6

Activation of human monocytes

Monocytes were isolated from "buffy coats" of citrated blood from healty blood donors.

Mononuclear cells were isolated as follows: "buffy coats" were diluted with 1 volume of cold RPMI 1640 and layered on the top of 15 ml of Ficoll-Paque in 50 ml Falcon tubes. After centrifugation at 400 xg for 30 minutes in a swingout rotor the layer between Ficoll-Paque and RPMI 1640-plasma (containing mononuclear cells and blood platelets) was removed, and the platelets were removed by washing 3 times (10 min.) at 100 xg.

The mononuclear cells were fractionated on a Percoll gradient: 10 xMEM and RPMI 1640 were added to a stock solution of Percoll (density: 1.13 g/ml) to make it isotonical with a density of 1.066 a/ml. A Percoll gradient was preformed by centrifugation at 3000 xg for 15 min. In a Hereaus medifuge with a 350° fixed angle rotor. On top of this gradient the mononuclear cells were layered and centrifugated at 2.700 xg for 20 minutes in a swingout rotor. In the upper band the monocytes were found with a purity of more than 90% as determined by non-specific esterase staining. The monocytes were cultivated at a density of $1 \times 10^6$ cells/ml in 24 well macrowell dishes in RPMI 1640 containing penicillin/Streptomoycin. The medium contained less than 6 pg/ml of endotoxin.

MRC-5 human lung embryo fibroblasts were cultivated in 96 well microwell plates in MEM with 2% FCS at a starting density of $1 \times 10^4$ cells/ml for 4 days before testing for mitogenic activity in monocyte culture meddium. The mitogenic activity in 100 µl of monocyte culture medium was determined by pulselabeling the MRX-5 cells with $^3$H-thymidine (1 µCi/ml) from 24 to 42 hours after addition of monocyte medium.

Results:

When monocytes are incubated with 5 ng HBP, a morphological change is observed after 1 and 2 days of incubation. The monocytes have become elongated (FIG. 4) in a similar manner to monocytes incubated with 100 ng/ml endotoxinin containing 1 mg/ml BSA (bovine serum albumin) (FIG. 5). The control cells do not have an activated morphology, as most cells still are uniformly round shaped (FIG. 6). The morphological changes of the monocytes are most clearly observed, when HBP is spotted and dried on the bottom of the well before the monocytes are added. This may indicate that immobilized HBP is superior to activate monocytes compared to non-immobilized HBP.

When culture medium from monocytes is tested for mitogenic activity towards MRC-5 human fibroblasts, monocytes incubated with HBP as described above for 2 days are found to secrete about twice the amount of mitogenic activity as control monocytes do. Monocytes incubated with 100 ng/ml LPS and 21 mg/ml BSA show about 5 times the mitogenic activity as control monocytes do.

EXAMPLE 7

Topical HBP formulation

HBP was formulated for topical administration in the following composition:

| Ingredients | % w/w |
|---|---|
| distilled water | 92.98 |
| hydroxyethylcellulose | 4.0 |
| sodium chloride | 0.41 |
| di-sodiumhydrogenphosphate-2hydrate | 0.83 |
| potassiumdihydrogenphosphate | 0.28 |
| gelatine, hydrolyzed | 0.5 |
| benzyl alcohol | 1.0 | to 10 9 of the above mentioned composition is added 250 ng HBP.

EXAMPLE 8

Injectable compositions which are suitable for parenteral administration of HBP contain stabilizers, salts, buffers, preservatives and mixtures thereof. A simple composition which stabilizes HBP sufficiently for its biological activity to be retained can be injected subcutaneously, intramuscularly or intraveneously.

Injectable composition

A formulation for parental administration of HBP was prepared with-the following composition:

| Ingredients | % w/w |
|---|---|
| glycine | 0.15 |
| de-sodiumhydrogenephosphate | 0.026 |
| sodiumdehydrogenephosphate | 0.026 |
| mannitol | 0.74 |
| distilled water | 100 |

The formulation may also contain 0.9% (v/v) benzyl alcohol is preservative. To 1 ml of the abovementioned composition is added 25 ng of HBP.

EXAMPLE 9

Effect of porcine HBP on wound healing in rats after local administration in wound chambers.

SUMMARY

In a wound healing experiment, four groups of twentyfive rats were equipped with wound chambers after removal of the skin on the nape of the neck down to the muscular fascia, in an area of about 15 mm in diameter. The groups were dosed locally with heparin-binding protein (HBP) 12.5 ng, 2.5 ng, 0.5 ng or placebo, twice daily for eight days. A solution of 0.9% saline with 0.1% rat albumin was used as a placebo and as a dissolution medium, and all doses were administered in 100 µl volumes. At the two highest dose levels, HBP had a significant accelerating effect on the wound healing, judged on the basis of the degree of epithelialization. The wounds in the top dose group were richly vascularized.

MATERIALS AND METHODS

Experimental animals 100 female Wistar rats, strain CRL:(W1)BR, approximately 240 g b.wt. and 80 days old were used. The rats were purchased from Charles River, BRD, and had been acclimatized for 6 days before use at 21±1° C., 60±10% relative humidity, air change 10 times per hour and daylight from 06.30 until 18.30 h. The rats were housed singly in rectangular Orth plastic cages with pine bedding. They were fed ad libitum Altromin diet 1324 and had free access to drinking water.

Operation

The rats were anaesthetized with pentobarbital, 50 mg/kg b.wt. intraperitoneally. They were shaved on the nape of the neck, and the operating field, 50 mm in diameter, was washed, disinfected and stripped with adhesive substance to remove small particles and hairs. Wound chambers consisting of an inner plastic ring and a nylon mesh in adhesive substance were pasted on the skin. The inner diameter of the wound chambers was 16 mm and the total diameter 45 mm. The nylon mesh was further fixated to the skin by 12 silk sutures, and the skin within the inner plastic ring was removed down to the muscular fascia. The wounds were covered with polyurethane lids pasted to the chambers with zinc plaster.

Postoperatively the rats were given TEMGESIC® (buprenorphin, obtained from Reckitt & Colman) 0.1 ml doses twice daily for three days.

Dosing pHBP was administered twice daily in 100 μl volumes of 0.9% NaCl solution with 0.1% rat albumin (sigma A4538). The dissolution medium was used as placebo.

Postoperatively the rats were randomized into four groups of 25 rats which were dosed as follows, once on the day of operation (day 1) and twice on day 2–8:

Group I: 12.5 ng pHBP
Group II: 0.5 ng pHBP
Group III: 2.5 ng pHBP
Group IV: Placebo The doses were administered locally just underneath the wound chamber lids. The cannulae were inserted through the polyurethane lids.

Observations

The rats were weighed on days 1, 3, 5, 7 and 9. On day 9 the wound chambers were removed during pentobarbital anaesthesia. The wounds were assessed macroscopically and photographed. The area of and around the operation site was dissected out and fixed in phosphate buffered neutral 4% formaldehyde for later histological examination. Finally, the rats were sacrificed by bleeding from the abdominal aorta. The blood was sampled for serum for IGF-I, PIIINP and hyaluronic acid analyses.

RESULTS

Table I shows the group mean body weights for the four groups of rats. All the rats lost weight post-operatively, the lowest weights being recorded on day 5. No significant intergroup differences in body weight were found.

As a result of the macroscopic examination of the wounds, the areas of the wounds and the areas covered with new epithelium on day 9 were calculated in the following way: The two diameters were measured, cranially-caudally and left-right, and the mean diameter ($D_{total}$) was used for calculating the total wound area:

$$\left(\frac{D_{total}}{2}\right)^2 \times 3.14 = \text{total area}.$$

The newly formed epithelium was measured from the edges, in the two places where it was widest and narrowest, respectively. The two results were added and subtracted from the $D_{total}$, giving the $D_{open}$ for the open wound.

The area for the open wound was calculated:

$$\left(\frac{D_{open}}{2}\right)^2 \times 3.14$$

and subtracted from the total area giving the area covered with new epithelium. This area was furthermore calculated as per cent of total area. In three rats dosed with 12.5 ng ×2 HBP, the unusual formation of epithelialized peninsulas in the open wound area were observed.

The results of the measurements and the calculated areas are shown in the enclosed data sheets. A survey of the results is given in Table II.

In many of the rats dosed with the highest dose of HBP (12.5 ng), a red haemorrhagic zone was observed just inside the epithelium edge and on the whole, the wounds seemed richly vascularized. A significantly higher degree of epithelialization was observed for this dose group and for the intermediate dose group (2.5 ng). The total wound area for the various groups was not significantly different from the area in the placebo group.

As the fibrin covering the wounds was removed with most of the wound chamber lids, lids+fibrin were fixed together with the tissues for histology.

CONCLUSION

On the basis of the macroscopic examination of the wounds, it can be concluded that HBP, 12.5 and 2.5 ng, administered twice daily, accelerated the wound healing significantly, as judged from the degree of epithelialization. The high degree of vascularization of the wounds in the top dose group is due to the angiogenic effect of HBP.

WOUND HEALING IN RATS

TABLE 1

Group mean body weights in female rats with wound chambers dosed with pHBP or placebo. The rats were operated day 1.

| Preparation and dose | No. rats | Body weight, g. means ± S.E.M. | | | | |
|---|---|---|---|---|---|---|
| | | Day 1 | Day 3 | Day 5 | Day 7 | Day 9 |
| pHBP, 12.5 ng twice daily | 23 | 249 ± 2 | 240 ± 3 | 233 ± 3 | 238 ± 3 | 242 ± 3 |
| pBHP, 0.5 ng twice daily | 24 | 245 ± 2 | 238 ± 2 | 228 ± 2 | 234 ± 2 | 239 ± 3 |
| pHBP, 2.5 ng twice daily | 24 | 245 ± 2 | 243 ± 3 | 232 ± 3 | 237 ± 3 | 240 ± 3 |
| Placebo (0.9% saline) with 0.1% rat albumin | 23 | 245 ± 2 | 240 ± 2 | 228 ± 2 | 233 ± 2 | 241 ± 2 |

WOUND HEALING IN RATS

TABLE II

Macroscopic data obtained with pHBP

| Experiment | Placebo | Dose of pHBP administered twice daily | Total area (mm2) means ± S.E.M. | Epithelialized wound area | |
|---|---|---|---|---|---|
| | | | | mm2 means ± S.E.M. | % of total area means ± S.E.M. |
| VII | 0.9% saline with 0.1% rat albumin | 12.5 ng | 118.3 6.3 | 52.2* 4.1 | 46.3** 3.6 |
| | | 2.5 ng | 144.3 7.8 | 53.3* 4.2 | 39.6 3.0 |
| | | 0.5 ng | 130.2 7.4 | 44.5 3.8 | 35.8 3.1 |
| | | (Placebo) | 125.1 6.2 | 38.5 4.2 | 31.6 3.4 |

| | WOUND HEALING VII | | Group I Epithelialized Wound Area | |
|---|---|---|---|---|
| | Wound Area (total) mm² | Open Wound Area mm² | mm² | % of total area |
| 1 | 132.73 | 92.10 | 40.63 | 30.61 |
| 2 | 165.13 | 103.87 | 61.26 | 37.10 |
| 3 | 143.14 | 61.88 | 81.26 | 56.77 |
| 4 | 153.94 | 50.27 | 103.67 | 67.35 |
| 5 | 86.59 | 33.18 | 53.41 | 61.68 |
| 6 | 165.13 | 122.72 | 42.41 | 25.68 |
| 7 Dead | | | | |
| 8 | 153.94 | 86.59 | 67.35 | 43.75 |
| 9 | 95.03 | 50.27 | 44.76 | 47.10 |
| 10 | 95.03 | 44.18 | 50.85 | 53.51 |

WOUND HEALING VII (continued)

| | Wound Area (total) mm² | Open Wound Area mm² | Epithelialized Wound Area mm² | % of total area |
|---|---|---|---|---|
| 11 | 113.10 | 70.88 | 42.22 | 37.33 |
| 12 | 78.54 | 50.27 | 28.27 | 35.99 |
| 13 | 143.14 | 122.72 | 20.42 | 14.27 |
| 14 | 78.54 | 28.27 | 50.27 | 64.01 |
| 15 | 132.73 | 103.87 | 28.86 | 21.74 |
| 16 | 122.72 | 95.03 | 27.69 | 22.56 |
| 17 | 122.72 | 63.62 | 59.10 | 48.16 |
| 18 | 95.03 | 28.27 | 66.76 | 70.25 |
| 19 | 103.87 | 40.18 | 63.69 | 61.32 |
| 20 | 56.75 | 12.57 | 44.18 | 77.85 |
| 21 | 143.14 | 103.87 | 39.27 | 27.44 |
| 22 | 95.03 | 50.27 | 44.76 | 47.10 |
| 23 Dead | | | | |
| 24 | 113.10 | 50.27 | 62.83 | 55.55 |
| 25 | 132.73 | 56.75 | 75.98 | 57.24 |
| X̄ | 118.34 | | 52.17* | 46.24** |
| S.E.M. | 6.26 | | 4.05 | 3.63 |

WOUND HEALING VII — Group II Epithelialized Wound Area

| | Wound Area (total) mm² | Open Wound Area mm² | mm² | % of total area |
|---|---|---|---|---|
| 26 | 201.06 | 165.12 | 35.93 | 17.87 |
| 27 | 132.73 | 86.59 | 46.14 | 34.76 |
| 28 | 113.10 | 86.59 | 26.51 | 23.44 |
| 29 | 188.69 | 113.10 | 75.59 | 40.06 |
| 30 | 132.73 | 95.03 | 37.70 | 28.40 |
| 31 | 103.87 | 70.88 | 32.99 | 31.76 |
| 32 | 143.14 | 70.88 | 72.26 | 50.48 |
| 33 | 103.87 | 44.18 | 59.69 | 57.47 |
| 34 | 122.72 | 50.27 | 72.45 | 59.04 |
| 35 | 50.27 | 28.27 | 22.00 | 43.76 |
| 36 | 132.73 | 65.75 | 75.98 | 57.24 |
| 37 | 103.87 | 78.54 | 25.33 | 24.39 |
| 38 | 95.03 | 56.75 | 38.28 | 40.28 |
| 39 | 95.03 | 63.62 | 31.41 | 33.05 |
| 40 | 86.59 | 28.27 | 58.32 | 67.35 |
| 41 | 153.94 | 113.10 | 40.84 | 26.53 |
| 42 | 113.10 | 70.88 | 42.22 | 37.33 |
| 43 | 176.71 | 153.94 | 22.77 | 12.89 |
| 44 | 103.87 | 86.59 | 17.28 | 16.64 |
| 45 | 143.14 | 78.54 | 64.60 | 45.13 |
| 46 | 143.14 | 95.03 | 48.11 | 33.61 |
| 47 | 143.14 | 103.87 | 39.27 | 27.44 |
| 48 Dead | | | | |
| 49 | 153.94 | 95.03 | 58.91 | 38.27 |
| 50 | 188.69 | 165.13 | 23.56 | 12.49 |
| X̄ | 130.21 | | 44.51 | 35.82 |
| S.E.M. | 7.37 | | 3.79 | 3.06 |

WOUND HEALING VII — Group III Epithelialized Wound Area

| | Wound Area (total) mm² | Open Wound Area mm² | mm² | % of total area |
|---|---|---|---|---|
| 51 | 132.73 | 95.03 | 37.70 | 28.40 |
| 52 | 63.62 | 44.18 | 19.44 | 30.56 |
| 53 | 201.06 | 122.72 | 78.34 | 38.96 |
| 54 | 132.73 | 56.75 | 75.98 | 57.24 |
| 55 | 103.87 | 44.18 | 59.69 | 57.47 |
| 56 | 153.94 | 70.88 | 63.06 | 53.96 |
| 57 | 165.13 | 70.88 | 94.75 | 57.08 |
| 58 | 153.94 | 78.54 | 75.40 | 48.98 |
| 59 | 132.73 | 78.54 | 54.19 | 40.83 |
| 60 | 86.59 | 38.48 | 48.11 | 55.56 |
| 61 | 113.10 | 50.27 | 62.83 | 55.55 |
| 62 | 226.98 | 188.69 | 38.29 | 16.87 |
| 63 | 122.72 | 78.54 | 44.18 | 36.00 |
| 64 | 132.73 | 113.10 | 19.63 | 14.79 |
| 65 | 122.72 | 70.88 | 51.84 | 42.24 |
| 66 | 176.71 | 143.14 | 33.57 | 19.00 |
| 67 | 153.94 | 78.54 | 75.40 | 48.98 |
| 68 | 153.94 | 95.03 | 58.91 | 38.27 |
| 69 | 201.06 | 132.73 | 68.33 | 33.98 |
| 70 | 113.10 | 63.62 | 49.48 | 43.75 |
| 71 | 176.71 | 153.94 | 22.77 | 12.89 |
| 72 | 176.71 | 132.73 | 43.98 | 24.98 |
| 73 | 113.10 | 78.54 | 34.56 | 30.56 |
| 74 Dead | | | | |
| 75 | 153.94 | 103.87 | 50.07 | 32.53 |
| X̄ | 144.33 | | 53.33* | 39.56 |
| S.E.M. | 7.75 | | 4.20 | 3.03 |

WOUND HEALING VII — Group IV Epithelialized Wound Area

| | Wound Area (total) mm² | Open Wound Area mm² | mm² | % of total area |
|---|---|---|---|---|
| 76 Dead | | | | |
| 77 | 103.87 | 70.88 | 32.99 | 31.76 |
| 78 | 95.03 | 56.75 | 38.28 | 40.28 |
| 79 | 95.03 | 38.48 | 56.55 | 59.51 |
| 80 | 70.88 | 50.27 | 70.61 | 29.08 |
| 81 | 132.73 | 56.75 | 75.98 | 57.24 |
| 82 | 86.59 | 63.62 | 22.97 | 26.53 |
| 83 | 113.10 | 95.03 | 18.07 | 15.98 |
| 84 | 176.71 | 153.94 | 22.77 | 12.89 |
| 85 | 113.10 | 78.54 | 34.56 | 30.56 |
| 86 Dead | | | | |
| 87 | 113.10 | 63.62 | 49.48 | 43.75 |
| 88 | 122.72 | 44.18 | 78.54 | 64.00 |
| 89 | 132.72 | 63.52 | 69.11 | 52.07 |
| 90 | 103.87 | 70.88 | 32.99 | 31.76 |
| 91 | 153.94 | 132.73 | 21.21 | 13.78 |
| 92 | 153.94 | 113.10 | 40.84 | 26.53 |
| 93 | 153.94 | 132.73 | 21.21 | 13.78 |
| 94 | 113.10 | 95.03 | 18.07 | 15.98 |
| 95 | 176.71 | 153.94 | 22.77 | 12.89 |
| 96 | 113.10 | 95.03 | 18.07 | 15.98 |
| 97 | 153.94 | 78.54 | 75.40 | 48.98 |
| 98 | 132.73 | 103.87 | 28.86 | 21.74 |
| 99 | 176.71 | 132.73 | 43.98 | 24.89 |
| 100 | 113.10 | 70.88 | 42.22 | 37.33 |
| X̄ | 126.12 | | 38.50 | 31.62 |
| S.E.M. | 6.20 | | 4.19 | 3.37 |

WOUND EXPERIMENT - MACROSCOPIC EVALUATION

| Rat No. | Wound diameter (mm) 1 | 2 | X̄ | Epithelium edge (mm) 1 | 2 | Open wound, diameter (mm) |
|---|---|---|---|---|---|---|
| 1 | 14 | 12 | 13 | 0.5 | 0.5 | 12 |
| | | | | | | (−7 × 3 mm) |
| 2 | 15 | 14 | 14.5 | 2 | 1 | 11.5 |
| 3 | 15 | 12 | 13.5 | 3 | 1 | 9.5 |
| | | | | | | (−3 × 3 mm) |
| 4 | 14 | 14 | 14 | 5 | 1 | 8 |
| 5 | 11 | 10 | 10.5 | 3 | 1 | 6.5 |
| 6 | 15 | 14 | 14.5 | 2 | 0 | 12.5 |
| 7 Dead | | | | | | |
| 8 | 14 | 14 | 14 | 3 | 0.5 | 10.5 |
| 9 | 11 | 11 | 11 | 2 | 1 | 8 |
| 10 | 13 | 9 | 11 | 3 | 0.5 | 7.5 |
| 11 | 14 | 10 | 12 | 2 | 0.5 | 9.5 |
| 12 | 10 | 10 | 10 | 1.5 | 0.5 | 8 |
| 13 | 13 | 14 | 13.5 | 0.5 | 0.5 | 12.5 |
| 14 | 10 | 10 | 10 | 3 | 1 | 6 |
| 15 | 13 | 13 | 13 | 1 | 0.5 | 11.5 |
| 16 | 12 | 13 | 12.5 | 1 | 0.5 | 11 |
| 17 | 13 | 12 | 12.5 | 3 | 0.5 | 9 |
| 18 | 12 | 10 | 11 | 4 | 1 | 6 |
| 19 | 12 | 11 | 11.5 | 2 | 2 | 7.5 |
| | | | | | | (−2 × 2 mm) |
| 20 | 8 | 9 | 8.5 | 4 | 0.5 | 4 |
| 21 | 13 | 14 | 13.5 | 1 | 1 | 11.5 |
| 22 | 11 | 11 | | 2 | 1 | 8 |
| 23 Dead | | | | | | |
| 24 | 12 | 12 | 12 | 4 | 0 | 8 |
| 25 | 13 | 13 | 13 | 3 | 1.5 | 8.5 |
| 26 | 16 | 16 | 16 | 1 | 0.5 | 14.5 |
| 27 | 12 | 14 | 13 | 1.5 | 1 | 10.5 |

WOUND EXPERIMENT - MACROSCOPIC EVALUATION

| Rat No. | Wound diameter (mm) 1 | 2 | $\bar{X}$ | Epithelium edge (mm) 1 | 2 | Open wound, diameter (mm) |
|---|---|---|---|---|---|---|
| 28 | 12 | 12 | 12 | 1 | 0.5 | 10.5 |
| 29 | 16 | 15 | 15.5 | 3 | 0.5 | 12 |
| 30 | 13 | 13 | 13 | 1 | 1 | 11 |
| 31 | 12 | 12 | 11.5 | 1.5 | 0.5 | 9.5 |
| 32 | 14 | 13 | 13.5 | 2 | 2 | 9.5 |
| 33 | 11 | 12 | 11.5 | 2 | 2 | 7.5 |
| 34 | 14 | 11 | 12.5 | 4 | 0.5 | 8 |
| 35 | 8 | 8 | 8 | 1.5 | 0.5 | 6 |
| 36 | 13 | 13 | 13 | 2.5 | 2 | 8.5 |
| 37 | 13 | 10 | 11.5 | 1 | 0.5 | 10 |
| 38 | 11 | 11 | 11 | 2 | 0.5 | 8.5 |
| 39 | 10 | 12 | 11 | 1.5 | 0.5 | 9 |
| 40 | 12 | 9 | 10.5 | 2 | 2.5 | 6 |
| 41 | 14 | 14 | 14 | 1.5 | 0.5 | 12 |
| 42 | 12 | 12 | 12 | 2.5 | 0.5 | 9.5 |
| 43 | 15 | 15 | 15 | 0.5 | 0.5 | 14 |
| 44 | 11 | 12 | 11.5 | 1 | 0 | 10.5 |
| 45 | 15 | 12 | 13.5 | 2.5 | 1 | 10 |
| 46 | 14 | 13 | 13.5 | 2 | 0.5 | 11 |
| 47 | 14 | 13 | 13.5 | 2 | 0 | 11.5 |
| 48 Dead | | | | | | |
| 49 | 15 | 13 | 14 | 3 | 0 | 11 |
| 50 | 16 | 15 | 15.5 | 0.5 | 0.5 | 14.5 |
| 51 | 14 | 12 | 13 | 1 | 1 | 11 |
| 52 | 9 | 9 | 9 | 1 | 0.5 | 7.5 |
| 53 | 16 | 16 | 16 | 3 | 1 | 8.5 |
| 54 | 14 | 12 | 13 | 3.5 | 1 | 8.5 |
| 55 | 12 | 11 | 11.5 | 2.5 | 1.5 | 7.5 |
| 56 | 14 | 14 | 14 | 3.5 | 1 | 9.5 |
| 57 | 15 | 14 | 14.5 | 4 | 1 | 9.5 |
| 58 | 15 | 13 | 14 | 3.5 | 0.5 | 10 |
| 59 | 13 | 13 | 13 | 3 | 0 | 10 |
| 60 | 11 | 10 | 10.5 | 3 | 0.5 | 7 |
| 61 | 12 | 12 | 12 | 4 | 0 | 8 |
| 62 | 17 | 17 | 17 | 1 | 0.5 | 15.5 |
| 63 | 13 | 12 | 12.5 | 2 | 0.5 | 10 |
| 64 | 12 | 14 | 13 | 1 | 0 | 12 |
| 65 | 14 | 11 | 12.5 | 3 | 0 | 9.5 |
| 66 | 15 | 15 | 15 | 1 | 0.5 | 13.5 |
| 67 | 14 | 14 | 14 | 2 | 2 | 10 |
| 68 | 13 | 15 | 14 | 2 | 1 | 11 |
| 69 | 16 | 16 | 16 | 2 | 1 | 13 |
| 70 | 12 | 12 | 12 | 2 | 1 | 9 |
| 71 | 15 | 15 | 15 | 0.5 | 0.5 | 14 |
| 72 | 16 | 14 | 15 | 1.5 | 0.5 | 13 |
| 73 | 12 | 12 | 12 | — | — | 10 |
| 74 Dead | | | | | | |
| 75 | 15 | 13 | 14 | 2 | 0.5 | 11.5 |
| 76 Dead | | | | | | |
| 77 | 11 | 12 | 11.5 | 2 | 0 | 9.5 |
| 78 | 11 | 11 | 11 | 2 | 0.5 | 8.5 |
| 79 | 10 | 12 | 11 | 2 | 2 | 7 |
| 80 | 10 | 9 | 9.5 | 1.5 | 0 | 8 |
| 81 | 13 | 13 | 13 | 3 | 1.5 | 8.5 |
| 82 | 12 | 9 | 10.5 | 1 | 0.5 | 9 |
| 83 | 13 | 11 | 12 | 1 | 0 | 11 |
| 84 | 15 | 15 | 15 | 0.5 | 0.5 | 14 |
| 85 | 12 | 12 | 12 | 2 | 0 | 10 |
| 86 Dead | | | | | | |
| 87 | 13 | 11 | 12 | 2 | 1 | 9 |
| 88 | 12 | 13 | 12.5 | 3 | 2 | 7.5 |
| 89 | 13 | 13 | 13 | 3 | 1 | 9 |
| 90 | 12 | 11 | 11.5 | 2 | 0 | 9.5 |
| 91 | 14 | 14 | 14 | 1 | 0 | 13 |
| 92 | 14 | 14 | 14 | 2 | 0 | 12 |
| 93 | 14 | 14 | 14 | 0.5 | 0.5 | 13 |
| 94 | 14 | 10 | 12 | 1 | 0 | 11 |
| 95 | 14 | 16 | 15 | 0.5 | 0.5 | 14 |
| 96 | 13 | 13 | 13 | 1 | 1 | 11 |
| 97 | 14 | 14 | 14 | 3 | 1 | 10 |
| 98 | 13 | 13 | 13 | 1 | 0.5 | 11.5 |
| 99 | 14 | 16 | 15 | 1.5 | 0.5 | 13 |
| 100 | 11 | 13 | 12 | 2 | 0.5 | 9.5 |

Histological Evaluation

Materials:

A 5 μm thick slice is cut out in the centre (craniocaudal) from the paraffin embedded wound.

The slice is stained in hematoxylin-cosin and evaluated in light microscope.

Results:

As a result of the microscopic examination of the wounds, the new epithelium on day 9 was calculated in the following way:

The diameter of the total wound was measured and the diameter of the open wound was measured and subtracted:

$$\frac{\text{Total wound} - \text{Open wound}}{2} = \text{new epithelium}$$

A rating scale was used to combine a quantitative and a qualitative histological evaluation of the wound healing in rats:

$$\frac{\text{new epithelium (mm)} + \left(\begin{array}{c}\text{evaluation of granulation tissue (0-4)} + \text{giant cells (0-4)}\end{array}\right) + \left(\begin{array}{c}\text{height granulation tissue (mm)} + \text{evaluation of epithelium (0-4)}\end{array}\right)}{4} = \text{rating}$$

The areas of the wounds and the areas covered with new epithelium on day 9 were calculated in the following way:

$$\text{Total area} = \left(\frac{\text{total wound diameter}}{2}\right)^2 \times 3.14$$

New epithelium area =

$$\text{Total area} = \left(\frac{\text{open wound diameter}}{2}\right)^2 \times 3.14$$

and the new epithelium area was furthermore calculated as per cent of total area.

The results of the measurements and the calculated ratings and areas are as shown in the Tables.

CONCLUSION

On the basis of the microscopic examination of the wounds and the evaluation of the data in the rating scale, it may be concluded that p-HBP, doses 12.5 ng and 0.5 ng, has an effect on the wound healing.

The effect is seen on the granulation tissues which are high in group 1 and 2, doses 12.5 ng and 0.5 ng pHBP (table II). In group 1, dose 12.5 ng pHBP, the granulation tissues are more mature compared to the placebo group (table II). From the area calculation the degree of epithelialization shows no significant difference between the groups.

WOUND HEALING EXPERIMENT VII

TABLE 1

Microscopic data obtained with pHBP

| Group | Rating scale Mean ± S.E.M. |
|---|---|
| 1 | |
| 12.5 ng p-HBP | 2.53*** 0.06 |
| 2 | |
| 0,5 ng p-HBP | 2.35* 0.07 |
| 3 | |
| 2.5 ng p-HBP | 2.26 0.07 |
| 4 | |
| Placebo | 2.10 0.09 |

***$p < 0.001$ levels of significant difference from placebo
**$p < 0.01$
*$p < 0.05$

TABLE II

| Group | | Total wound (mm) | Open wound (mm) | Granulation tissue (0–4) | Giant cells (0–4) | Epithelium edge (mm) | Evaluation of epithelium (0–4) | Height of granulation tissue (mm) |
|---|---|---|---|---|---|---|---|---|
| 1 | X | 9.26* | 6.52 | 2.96* | 0.48* | 2.78 | 4.00 | 2.26** |
| 12.5 ng | Sd | 1.91 | 2.19 | 0.21 | 1.08 | 1.13 | 0.00 | 0.54 |
| HBP | SEM | 0.40 | 0.46 | 0.04 | 0.23 | 0.23 | 0.00 | 0.11 |
| 2 | X | 9.33* | 6.88* | 2.58 | 0.58* | 2.46 | 4.00 | 2.17** |
| 0.5 ng | Sd | 1.86 | 2.33 | 0.50 | 1.06 | 1.22 | 0.00 | 0.56 |
| p-HBP | SEM | 0.38 | 0.48 | 0.10 | 0.22 | 0.25 | 0.00 | 0.12 |
| 3 | X | 8.88 | 6.54 | 2.63 | 0.63 | 2.33 | 4.00 | 1.88 |
| 2.5 ng | Sd | 2.11 | 2.06 | 0.49 | 1.28 | 1.13 | 0.00 | 0.61 |
| p-HBP | SEM | 0.43 | 0.42 | 0.10 | 0.26 | 0.23 | 0.00 | 0.13 |
| 4 | X | 8.22 | 5.39 | 2.70 | 1.39 | 2.83 | 4.00 | 1.70 |
| Placebo | Sd | 1.35 | 1.85 | 0.47 | 1.50 | 1.34 | 0.00 | 0.56 |
| | SEM | 0.27 | 0.39 | 0.10 | 0.31 | 0.28 | 0.00 | 0.12 |

***$p < 0.001$ levels of significant difference from placebo
**$p < 0.01$
*$p < 0.05$

We claim:

1. A purified and isolated porcine heparin-binding protein having the following amino acid sequence

```
1              5              10             15
Ile-Val-Gly-Gly-Arg-Arg-Ala-Gln-Pro-Gln-Glu-Phe-Pro-Phe-Leu-Ala-Ser-
                                                              20
                                                         -Ile-Gln-Lys-
21             25             30             35
Gln-Gly-Arg-Pro-Phe-Cys-Ala-Gly-Ala-Leu-Val-His-Pro-Arg-Phe-Val-
                                                              40
                                                    -Leu-Thr-Ala-Ala-
41             45             50             55
Ser-Cys-Phe-Arg-Gly-Lys-Asn-Ser-Gly-Ser-Ala-Ser-Val-Val-Leu-Gly-
                                                              60
                                                         -Ala-Tyr-Asp-Leu-
61             65             70             75
Arg-Gln-Gln-Glu-Gln-Ser-Arg-Gln-Thr-Phe-Ser-Ile-Arg-Ser-Ile-Ser-Gln-
                                                              80
                                                         -Asn-Gly-Tyr-
81             85             90             95
Asp-Pro-Arg-Gln-Asn-Leu-Asn-Asp-Val-Leu-Leu-Leu-Gln-Leu-Asp-Arg-
                                                              100
                                                         -Glu-Ala-Arg-Leu-
                                         CHO
101            105            110        \  115
Thr-Pro-Ser-Val-Ala-Leu-Val-Pro-Leu-Pro-Pro-Gln-Asx-Ala-Thr-Val-
                                                              120
                                                         -Glu-Ala-Gly-Thr-
121            125            130
Asn-Cys-Gln-Val-Ala-Gly-Trp-Gly-Thr-Gln-Arg-
                                         135            140
                               -Leu-Arg-Arg-Leu-Phe-Ser-Arg-Phe-Pro-
             CHO
141          \ 145            150
Arg-Val-Leu-Asx-Val-Thr-Val-Thr-Ser-Asn-Pro-
                              155            160
                     -Cys-Leu-Pro-Arg-Asp-Met-Cys-Ile-Gly-
161            165            170
Val-Phe-Ser-Arg-Arg-Gly-Arg-Ile-Ser-Gln-Gly-
                                         175            180
                              -Asp-Arg-Gly-Thr-Pro-Leu-Val-Cys-Asn-
181            185            190            195
Gly-Leu-Ala-Gln-Gly-Val-Ala-Ser-Phe-Leu-Arg-Arg-Arg-Phe-Arg-Arg-
                                                              200
                                                         -Ser-Ser-Gly-Phe-
```

```
            201         205          210         215
Phe-Thr-Arg-Val-Ala-Leu-Phe-Arg-Asn-Trp-Ile-Asp-Ser-Val-Leu-Asn-

219
                                        -Asn-Pro-Pro.
```

2. A therapeutic preparation comprising a therapeutically active amount of the heparin-binding protein of claim 1 and a pharmaceutically acceptable carrier.

3. A method for activating monocytes in a mammal comprising administering to the mammal the heparin-binding protein of claim 1 in an amount effective to activate said monocytes.

4. A method for activating monocytes in a mammal in need thereof comprising administering to the mammal an isolated and purified human heparin-binding protein having the amino acid sequence of wherein Xxx at position 222 is Pro or absent, and Xxx at position 223 is Gly or absent, in an amount effective to activate said monocytes.

5. A method for stimulating angiogenesis in a mammal in need thereof, comprising administering to the mammal the heparin-binding protein of claim 1 in an amount effective to stimulate said angiogenesis.

6. A method for stimulating angiogenesis in a mammal in need thereof, comprising administering to the mammal a purified and isolated human heparin-binding protein having the amino acid sequence of

```
 1                                                                                                    20
Ile — Val— Gly— Gly— Arg—Lys— Ala— Arg—Pro— Arg—Gln— Phe— Pro— Phe—Leu—Ala— Ser— Ile — Gln—Asn 21             25                      30                      35                      40
Gln— Gly—Arg— His— Phe—Cys—Gly— Gly— Ala—Leu— Ile — His— Ala— Arg—Phe— Val— Met—Thr— Ala— Ala 41             45                      50                      55                      60
Ser— Cys—Phe— Gln— Ser— Gln—Asn—Pro— Gly— Val— Ser— Thr— Val— Val— Leu—Gly—Ala— Tyr— Asp—Leu 61             65                      70                      75                      80
Arg—Arg—Arg— Glu— Arg—Gln— Ser— Arg—Gln— Thr— Phe— Ser— Ile — Ser— Ser— Met—Ser— Glu—Asn—Gly

CHO
 81             85                      90                      95                        \
Tyr— Asp—Pro— Gln— Gln—Asn—Leu— Asn—Asp—Leu— Met—Leu— Leu—Gln— Leu—Asp—Arg— Glu— Ala— Asx

CHO                                            CHO
101        \   105                     110                \   115                       120
Leu—Thr— Ser— Asx— Val— Thr— Ile — Leu—Pro— Leu—Pro— Leu— Gln— Asx—Ala— Thr— Val— Glu—Ala— Gly 121            125                     130                     135                      140
Thr— Arg—Cys— Gln— Val— Ala— Gly— Trp— Gly— Ser— Gln—Arg— Ser— Gly— Gly—Arg— Leu— Ser— Arg—Phe

CHO
141         \                          150                     155
Pro— Arg—Phe— Val— Asx— Val— Thr— Val— Thr—Pro— Glu—Asp—Gln— Cys— Arg—Pro— Asn—Asn—Val— Cys 161            165                     170                     175                      180
Thr— Gly— Val— Leu—Thr— Arg—Arg—Gly— Gly— Ile — Cys—Asn—Gly— Asp—Gly— Gly— Thr— Pro— Leu—Val 185                     190                     195                      200
Cys— Glu—Gly— Leu— Ala— His— Gly— Val— Ala— Ser— Phe— Ser— Leu—Gly— Pro— Cys—Gly—Arg—Gly— Pro 201            205                     210                     215                      220
Asp—Phe— Phe— Thr— Arg—Val— Ala—Leu—Phe—Arg—Asp—Trp— Ile — Asp—Gly— Val— Leu—Asn—Asn—Pro 221 222 223
Gly— Xxx—Xxx
```

| 1 | | | | | | | | | | | | | | | | | | | 20 |
|---|---|---|---|---|---|---|---|---|---|---|---|---|---|---|---|---|---|---|---|
| Ile — Val — Gly — Gly — Arg — Lys — Ala — Arg — Pro — Arg — Gln — Phe — Pro — Phe — Leu — Ala — Ser — Ile — Gln — Asn |

21 — Gln—Gly—Arg—His—Phe—Cys—Gly—Gly—Ala—Leu—Ile—His—Ala—Arg—Phe—Val—Met—Thr—Ala—Ala — 40

41 — Ser—Cys—Phe—Gln—Ser—Gln—Asn—Pro—Gly—Val—Ser—Thr—Val—Val—Leu—Gly—Ala—Tyr—Asp—Leu — 60

61 — Arg—Arg—Arg—Glu—Arg—Gln—Ser—Arg—Gln—Thr—Phe—Ser—Ile—Ser—Ser—Met—Ser—Glu—Asn—Gly — 80

81 — Tyr—Asp—Pro—Gln—Gln—Asn—Leu—Asn—Asp—Leu—Met—Leu—Leu—Gln—Leu—Asp—Arg—Glu—Ala—Asx (CHO) — 100

101 — Leu—Thr—Ser—Asx(CHO)—Val—Thr—Ile—Leu—Pro—Leu—Pro—Leu—Gln—Asx(CHO)—Ala—Thr—Val—Glu—Ala—Gly — 120

121 — Thr—Arg—Cys—Gln—Val—Ala—Gly—Trp—Gly—Ser—Gln—Arg—Ser—Gly—Gly—Arg—Leu—Ser—Arg—Phe — 140

141 — Pro—Arg—Phe—Val—Asx(CHO)—Val—Thr—Val—Thr—Pro—Glu—Asp—Gln—Cys—Arg—Pro—Asn—Asn—Val—Cys — 160

161 — Thr—Gly—Val—Leu—Thr—Arg—Arg—Gly—Gly—Ile—Cys—Asn—Gly—Asp—Gly—Gly—Thr—Pro—Leu—Val — 180

181 — Cys—Glu—Gly—Leu—Ala—His—Gly—Val—Ala—Ser—Phe—Ser—Leu—Gly—Pro—Cys—Gly—Arg—Gly—Pro — 200

201 — Asp—Phe—Phe—Thr—Arg—Val—Ala—Leu—Phe—Arg—Asp—Trp—Ile—Asp—Gly—Val—Leu—Asn—Asn—Pro — 220

221 222 223
Gly—Xxx—Xxx wherein Xxx at position 222 is Pro or absent, and Xxx at position 223 is Gly or absent, in an amount effective to stimulate said angiogenesis.

7. A method for stimulating tissue repair in a wound of a mammal in need thereof, comprising administering to the mammal the heparin-binding protein of claim 1 in an amount effective to stimulate said tissue repair.

8. A method for stimulating tissue repair in a wound of a mammal in need thereof, comprising administering to the mammal a purified and isolated human heparin-binding protein having the amino acid sequence of 1 — Ile — Val — Gly — Gly — Arg — Lys — Ala — Arg — Pro — Arg — Gln — Phe — Pro — Phe — Leu — Ala — Ser — Ile — Gln — Asn — 20

21 — Gln—Gly—Arg—His—Phe—Cys—Gly—Gly—Ala—Leu—Ile—His—Ala—Arg—Phe—Val—Met—Thr—Ala—Ala — 40

41 — Ser—Cys—Phe—Gln—Ser—Gln—Asn—Pro—Gly—Val—Ser—Thr—Val—Val—Leu—Gly—Ala—Tyr—Asp—Leu — 60

61 — Arg—Arg—Arg—Glu—Arg—Gln—Ser—Arg—Gln—Thr—Phe—Ser—Ile—Ser—Ser—Met—Ser—Glu—Asn—Gly — 80

```
                                                CHO
81          85              90              95   \
Tyr—Asp—Pro—Gln—Gln—Asn—Leu—Asn—Asp—Leu—Met—Leu—Leu—Gln—Leu—Asp—Arg—Glu—Ala—Asx

CHO                         CHO
101      \   105             110     \   115             120
Leu—Thr—Ser—Asx—Val—Thr—Ile—Leu—Pro—Leu—Pro—Leu—Gln—Asx—Ala—Thr—Val—Glu—Ala—Gly 121         125             130             135             140
Thr—Arg—Cys—Gln—Val—Ala—Gly—Trp—Gly—Ser—Gln—Arg—Ser—Gly—Gly—Arg—Leu—Ser—Arg—Phe

CHO
141          \              150             155             160
Pro—Arg—Phe—Val—Asx—Val—Thr—Val—Thr—Pro—Glu—Asp—Gln—Cys—Arg—Pro—Asn—Asn—Val—Cys 161         165             170             175             180
Thr—Gly—Val—Leu—Thr—Arg—Arg—Gly—Gly—Ile—Cys—Asn—Gly—Asp—Gly—Gly—Thr—Pro—Leu—Val 185             190             195             200
Cys—Glu—Gly—Leu—Ala—His—Gly—Val—Ala—Ser—Phe—Ser—Leu—Gly—Pro—Cys—Gly—Arg—Gly—Pro 201         205             210             215             220
Asp—Phe—Phe—Thr—Arg—Val—Ala—Leu—Phe—Arg—Asp—Trp—Ile—Asp—Gly—Val—Leu—Asn—Asn—Pro 221 222 223
Gly—Xxx—Xxx
``` wherein Xxx at position 222 is Pro or absent, and Xxx at position 223 is Gly or absent, in an amount effective to stimulate said tissue repair.

9. A method for treating a tumor in a mammal in need thereof, comprising administering to the mammal the heparin-binding protein of claim 1 in an amount effective to recruit circulating monocytes to and be cytotoxic to said tumor.

10. A method for treating a tumor in a mammal in need thereof, comprising administering to the mammal an isolated and purified human heparin-binding protein having the acid sequence of

```
1                                                                       20
Ile—Val—Gly—Gly—Arg—Lys—Ala—Arg—Pro—Arg—Gln—Phe—Pro—Phe—Leu—Ala—Ser—Ile—Gln—Asn 21          25              30              35              40
Gln—Gly—Arg—His—Phe—Cys—Gly—Gly—Ala—Leu—Ile—His—Ala—Arg—Phe—Val—Met—Thr—Ala—Ala 41          45              50              55              60
Ser—Cys—Phe—Gln—Ser—Gln—Asn—Pro—Gly—Val—Ser—Thr—Val—Val—Leu—Gly—Ala—Tyr—Asp—Leu 61          65              70              75              80
Arg—Arg—Arg—Glu—Arg—Gln—Ser—Arg—Gln—Thr—Phe—Ser—Ile—Ser—Ser—Met—Ser—Glu—Asn—Gly

CHO
81          85              90              95                          \
Tyr—Asp—Pro—Gln—Gln—Asn—Leu—Asn—Asp—Leu—Met—Leu—Leu—Gln—Leu—Asp—Arg—Glu—Ala—Asx

CHO                         CHO
101      \   105             110     \   115             120
Leu—Thr—Ser—Asx—Val—Thr—Ile—Leu—Pro—Leu—Pro—Leu—Gln—Asx—Ala—Thr—Val—Glu—Ala—Gly 121         125             130             135             140
Thr—Arg—Cys—Gln—Val—Ala—Gly—Trp—Gly—Ser—Gln—Arg—Ser—Gly—Gly—Arg—Leu—Ser—Arg—Phe

CHO
141          \              150             155             160
Pro—Arg—Phe—Val—Asx—Val—Thr—Val—Thr—Pro—Glu—Asp—Gln—Cys—Arg—Pro—Asn—Asn—Val—Cys 161         165             170             175             180
Thr—Gly—Val—Leu—Thr—Arg—Arg—Gly—Gly—Ile—Cys—Asn—Gly—Asp—Gly—Gly—Thr—Pro—Leu—Val 185             190             195             200
Cys—Glu—Gly—Leu—Ala—His—Gly—Val—Ala—Ser—Phe—Ser—Leu—Gly—Pro—Cys—Gly—Arg—Gly—Pro
```

```
201                         205                              210                           215                          220
Asp—Phe—Phe—Thr—Arg—Val—Ala—Leu—Phe—Arg—Asp—Trp—Ile—Asp—Gly—Val—Leu—Asn—Asn—Pro 221  222  223
Gly—Xxx—Xxx
``` wherein Xxx at position 222 is Pro or absent, and Xxx at position 223 is Gly or absent, in an amount effective to recruit circulating monocytes to and be cytotoxic to said tumor.

* * * * *